United States Patent [19]
Yoshikawa et al.

[11] Patent Number: 6,040,258
[45] Date of Patent: Mar. 21, 2000

[54] ZEOLITE CIT-5 AND METHOD OF MAKING

[75] Inventors: Masahito Yoshikawa, Nagoya, Japan; Mark E. Davis, Pasadena, Calif.

[73] Assignee: California Institute of Technology, Pasadena, Calif.

[21] Appl. No.: 09/119,806

[22] Filed: Jul. 21, 1998

Related U.S. Application Data

[63] Continuation-in-part of application No. 08/910,770, Aug. 13, 1997.

[51] Int. Cl.$^7$ ...................................................... B01J 29/06
[52] U.S. Cl. .............................. 502/64; 502/68; 423/702; 423/704; 423/705; 423/707; 423/708; 423/718; 423/328.2; 423/329.1
[58] Field of Search ........................ 502/64, 68; 423/702, 423/704, 705, 707, 708, 718, 328.2, 329.1

[56] References Cited

U.S. PATENT DOCUMENTS

| | | | |
|---|---|---|---|
| 4,936,977 | 6/1990 | Zones et al. | 208/111 |
| 5,271,922 | 12/1993 | Nakagawa | 423/702 |
| 5,580,540 | 12/1996 | Nakagawa | 423/718 |

FOREIGN PATENT DOCUMENTS

WO9522507A  8/1995  WIPO ............................ C01B 33/26

OTHER PUBLICATIONS

Wagner, Paul, et al.: "CIT–5: a high–silica zeolite with 14–ring pores", Chemical Communications, No. 22, Nov. 21, 1997, pp. 2179–2180, XP002086050 Ciety of Chemistry GB.

*Primary Examiner*—Walter D. Griffin
*Assistant Examiner*—Nadine Preisch
*Attorney, Agent, or Firm*—Richard J. Sheridan; Timothy J. Hadlock

[57] ABSTRACT

The present invention relates to new crystalline zeolite CIT-5 prepared using a N(16) methylsparteinium cation templating agent.

33 Claims, No Drawings

ZEOLITE CIT-5 AND METHOD OF MAKING

This application is a continuation-in-part of application Ser. No. 08/910,770, filed Aug. 13, 1997 which is incorporated herein by reference.

BACKGROUND OF THE INVENTION

1. Field of the Invention

The present invention relates to new crystalline zeolite CIT-5, a method for preparing CIT-5 using a N(16) methylsparteinium cation templating agent, and processes employing CIT-5 as a catalyst.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

SUMMARY OF THE INVENTION

The present invention is directed to a family of crystalline molecular sieves with unique properties, referred to herein as "zeolite CIT-5" or simply "CIT-5". Preferably, CIT-5 is obtained in its silicate or aluminosilicate form. The term "silicate" refers to a zeolite having a high mole ratio of silicon oxide relative to aluminum oxide, preferably a mole ratio greater than about 100. As used herein, the term "aluminosilicate" refers to a zeolite containing both alumina and silica.

In accordance with this invention, there is provided a zeolite comprising an oxide of a tetravalent element or mixture of oxides of tetravalent elements and, optionally, an oxide of a trivalent element or mixtures of oxides of trivalent elements and having, after calcination, the X-ray diffraction lines of Table II.

Further, in accordance with this invention, there is provided a zeolite comprising an oxide selected from silicon oxide, germanium oxide and mixtures thereof and an optional oxide selected from aluminum oxide, boron oxide, gallium oxide, iron oxide and mixtures thereof and having, after calcination, the X-ray diffraction lines of Table II below.

The present invention further provides such a zeolite having a composition, as synthesized and in the anhydrous state, in terms of mole ratios as follows:

$YO_2/W_aO_b > 40$
$M/YO_2 \leq 0.05$
$Q/YO_2 \leq 0.05$ wherein Y is silicon, germanium or a mixture thereof; W is aluminum, boron, gallium, iron or mixtures thereof; a=1 or 2, b=2 when a=1 (i.e., W is tetravalent) and b=3 when a=2 (i.e., W is trivalent); M is an alkali metal; and Q comprises a N(16) methylsparteinium cation.

In accordance with this invention, there is provided a zeolite comprising an oxide of silicon, germanium or mixtures thereof and an oxide of titanium and having, after calcination, the X-ray diffraction lines of Table II.

The present invention also provides a zeolite having a composition, as synthesized and in the anhydrous state, in terms of mole ratios as follows:

$YO_2/TiO_2 > 40$
$M/YO_2 \leq 0.05$
$Q/YO_2 \leq 0.05$ wherein Y is silicon, germanium or a mixture thereof; M is an alkali metal; and Q comprises a N(16) methylsparteinium cation.

In accordance with this invention, there is also provided a zeolite prepared by thermally treating a zeolite comprising an oxide selected from silicon oxide, germanium oxide and mixtures thereof and, optionally, an oxide selected from aluminum oxide, boron oxide, gallium oxide, iron oxide and mixtures thereof at a temperature of from about 200° C. to about 800° C., the thus-prepared zeolite having the X-ray diffraction lines of Table II. The present invention also includes this thus-prepared zeolite which is predominantly in the hydrogen form, which hydrogen form is prepared by ion exchanging with an acid or with a solution of an ammonium salt followed by a second calcination.

Also provided in accordance with the present invention is a method of preparing a crystalline material comprising an oxide of a tetravalent element or mixture of oxides of tetravalent elements and, optionally, an oxide of a trivalent element or mixtures of oxides of trivalent elements, said method comprising contacting in admixture under crystallization conditions sources of said oxides, a source of alkali metal and a templating agent comprising a N(16) methylsparteinium cation.

The present invention additionally provides a process for converting hydrocarbons comprising contacting a hydrocarbonaceous feed at hydrocarbon converting conditions with a catalyst comprising the zeolite of this invention. The zeolite may be predominantly in the hydrogen form, partially acidic or substantially free of acidity, depending on the process.

Further provided by the present invention is a hydrocracking process comprising contacting a hydrocarbon feedstock under hydrocracking conditions with a catalyst comprising the zeolite of this invention, preferably predominantly in the hydrogen form.

This invention also includes a dewaxing process comprising contacting a hydrocarbon feedstock under dewaxing conditions with a catalyst comprising the zeolite of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the zeolite of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising at least one Group VIII metal and the zeolite of this invention. The zeolite may be predominantly in the hydrogen form.

In accordance with this invention, there is also provided a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and the zeolite of this invention, preferably predominantly in the hydrogen form. The catalyst may be a layered catalyst comprising a first layer comprising at least one Group VIII metal and the zeolite of this invention, and a second layer comprising an aluminosilicate zeolite which is more shape selective than the zeolite of said first layer.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and the zeolite of this invention. The zeolite may be predominantly in the hydrogen form.

Further included in this invention is a process for isomerization dewaxing a raffinate comprising contacting said raffinate in the presence of added hydrogen with a catalyst comprising at least one Group VIH metal and the zeolite of this invention. The raffinate may be bright stock, and the zeolite may be predominantly in the hydrogen form.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the zeolite of this invention made substantially free of acidity by neutralizing said zeolite with a basic metal. Also provided in this invention is such a process wherein the zeolite contains a Group VIII metal component.

Also provided by the present invention is a catalytic cracking process comprising contacting a hydrocarbon feedstock in a reaction zone under catalytic cracking conditions in the absence of added hydrogen with a catalyst comprising the zeolite of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the zeolite of this invention, preferably predominantly in the hydrogen form. The zeolite may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the zeolite of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the zeolite of this invention, preferably predominantly in the hydrogen form. The aromatic hydrocarbon and the polyalkyl aromatic hydrocarbon may be present in a molar ratio of from about 1:1 to about 25:1, respectively. The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the zeolite of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the zeolite of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the zeolite of this invention.

The present invention further provides a process for oligomerizing olefins comprising contacting an olefin feed under oligomerization conditions with a catalyst comprising the zeolite of this invention.

This invention also provides a process for converting lower alcohols and other oxygenated hydrocarbons comprising contacting said lower alcohol or other oxygenated hydrocarbon with a catalyst comprising the zeolite of this invention under conditions to produce liquid products.

Also provided by the present invention is an improved process for the reduction of oxides of nitrogen contained in a gas stream in the presence of oxygen wherein said process comprises contacting the gas stream with a zeolite, the improvement comprising using as the zeolite, the zeolite of this invention. The zeolite may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

DETAILED DESCRIPTION OF THE INVENTION

In preparing CIT-5 zeolites, a N(16) methylsparteinium cation is used as a crystallization template. The N(16) methylsparteinium cation may have the following structure:

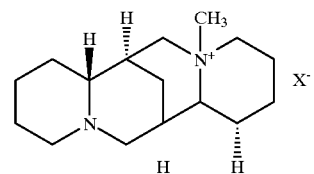

The anion (X) associated with the cation may be any anion which is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

The N(16) methylsparteinium cation may be prepared as described in Lobo and Davis, "Synthesis and Characterization of Pure-Silica and Boron-Substituted SSZ-24 Using N(16) methylsparteinium Bromide as Structure-Directing Agent", *Microporous Materials* 3 (1994), pp. 61–69, Elsevier.

In general, CIT-5 is prepared by contacting an active source of one or more oxides selected from the group consisting of alkali metal oxide, trivalent element oxide(s), and tetravalent element oxide(s) with the N(16) methylsparteinium cation templating agent.

CIT-5 is prepared from a reaction mixture having the composition shown in Table A below.

TABLE A

| | Reaction Mixture | |
|---|---|---|
| | Typical | Preferred (*) |
| $YO_2/W_aO_b$ | 15–∞ | 25–∞ |
| $OH^-/YO_2$ | 0.1–0.5 | 0.2–0.45 (0.3) |
| $Q/YO_2$ | 0.1–0.3 | 0.15–0.25 (0.2) |
| $M/YO_2$ | 0.02–0.3 | 0.05–0.2 (0.1) |
| $H_2O/YO_2$ | 15–200 | 30–100 (40) |

*Numbers in parentheses represent quantitites believed to be optimal. where Y, W, a, b, M and Q are as defined above.

It should be emphasized that CIT-5 can be made in its all-silica form, i.e., where a source of another oxide is not intentionally added to the reaction mixture. In this case, $YO_2/W_aO_b$ would be at or near ∞.

In practice, CIT-5 is prepared by a process comprising:

(a) preparing an aqueous solution containing sources of at least one oxide capable of forming a crystalline molecular sieve and a N(16) methylsparteinium cation having an anionic counterion which is not detrimental to the formation of CIT-5;

(b) maintaining the aqueous solution under conditions sufficient to form crystals of CIT-5; and (c) recovering the crystals of CIT-5.

Accordingly, CIT-5 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides of a tetravalent element(s), and, optionally, one or a combination of a trivalent element(s). The tetravalent element(s) is preferably selected from the group consisting of silicon, germanium and combinations thereof. More preferably, the tetravalent element is silicon. The trivalent element is preferably aluminum, boron, gallium, or iron. In terms of reaction speed, gallium is preferred. However, in some catalytic applications, aluminum is preferred.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides.

A source zeolite reagent may provide a source of aluminum. In most cases, the source zeolite also provides a source of silica. The source zeolite in its dealuminated or form may also be used as a source of silica, with additional silicon added using, for example, the conventional sources listed above. Use of a source zeolite reagent as a source of alumina for the present process is more completely described in U.S. Pat. No. 5,225,179, issued Jul. 6, 1993 to Zones et al. entitled "Method of Making Molecular Sieves", the disclosure of which is incorporated herein by reference.

An alkali metal is added to the reaction mixture. A variety of sources can be used, such as alkali metal hydroxides and alkali metal carbonates. Lithium or a mixture of lithium and another alkali metal is preferred, with lithium hydroxide being particularly preferred. The lithium cation may be part of the as-synthesized crystalline oxide material, in order to balance valence electron charges therein. Other alkali metals which can be used include sodium and potassium, with the hydroxides being preferred. The alkali metal may be employed in an amount of from about 0.03 to about 0.15 mole of alkali metal per mole of silica (or other oxide(s) of a tetravalent element(s)).

It has been found that the inclusion of zinc in the reaction mixture can help prevent the formation of crystal phases other than the CIT-5. The zinc can be added as, e.g., zinc acetate dihydrate, in an amount of up to about 0.08, preferably about 0.04, mole of zinc acetate dihydrate per mole of silica (or other oxide(s) of a tetravalent element(s)).

The reaction mixture is maintained at an elevated temperature until the crystals of the CIT-5 zeolite are formed. The hydrothermal crystallization is usually conducted under autogenous pressure, at a temperature between 100° C. and 200° C., preferably between 135° C. and 160° C. The crystallization period is typically greater than 1 day and preferably from about 7 days to about 21 days.

During the hydrothermal crystallization step, the CIT-5 crystals can be allowed to nucleate spontaneously from the reaction mixture. The use of CIT-5 crystals as seed material can be advantageous in decreasing the time necessary for complete crystallization to occur. In addition, seeding can lead to an increased purity of the product obtained by promoting the nucleation and/or formation of CIT-5 over any undesired phases. When used as seeds, CIT-5 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized CIT-5 zeolite crystals. The drying step can be performed at atmospheric pressure or under vacuum.

CIT-5 has a composition, as synthesized and in the anhydrous state, in terms of mole ratios, shown in Table B below.

TABLE B

| As-Synthesized CIT-5 | |
|---|---|
| $YO_2/W_aO_b$ | >40 |
| $M/YO_2$ | ≤0.05 |
| $Q/YO_2$ | ≤0.05 | where Y, W, a, b, M and Q are as defined above. As noted above, CIT-5 can be in the all-silica form, in which case $YO_2/W_aO_b$ would be at or near ∞.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

It is believed that CIT-5 is comprised of a new framework structure or topology which is characterized by its X-ray diffraction pattern. CIT-5 zeolites, as-synthesized, have a crystalline structure whose X-ray powder diffraction pattern typically exhibits the characteristic lines shown in Table I and are thereby distinguished from other known zeolites.

TABLE I

As-Synthesized All-Silica CIT-5

| 2 Theta[a] | d | Relative Intensity[b] |
|---|---|---|
| 6.96 | 12.7 | VS |
| 7.29 | 12.12 | S |
| 12.81 | 6.905 | W |
| 13.93 | 6.353 | M |
| 18.96 | 4.676 | S |
| 19.59 | 4.528 | M |
| 20.00 | 4.436 | S |
| 20.50 | 4.329 | M–S |
| 20.95 | 4.236 | S–VS |
| 21.93 | 4.050 | W |
| 23.41 | 3.797 | W |
| 24.22 | 3.672 | W |
| 24.62 | 3.612 | M |
| 25.80 | 3.451 | W |
| 26.10 | 3.412 | W |
| 26.73 | 3.332 | S–VS |
| 27.11 | 3.286 | W |
| 28.22 | 3.159 | M |
| 29.38 | 3.038 | W |
| 29.82 | 2.994 | W |
| 31.37 | 2.849 | W |
| 31.55 | 2.833 | W |
| 32.99 | 2.713 | W |
| 33.98 | 2.636 | W |
| 35.33 | 2.538 | W |
| 35.64 | 2.517 | W |
| 36.42 | 2.465 | W |
| 37.03 | 2.426 | W |
| 37.70 | 2.384 | W |
| 38.73 | 2.323 | W |
| 44.70 | 2.026 | W |
| 49.42 | 1.843 | W |

[a]±0.15
[b]The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

After calcination, the CIT-5 zeolites have a crystalline structure whose X-ray powder diffraction pattern typically includes the characteristic lines shown in Table II:

TABLE II

Calcined CIT-5

| 2 Theta[a] | d | Relative Intensity |
|---|---|---|
| 6.95 | 12.7 | VS |
| 7.3 | 12.1 | S–VS |
| 13.9 | 6.37 | W–S |
| 19.0 | 4.67 | W–VS |
| 20.0 | 4.44 | M–VS |
| 20.5 | 4.33 | W–S |
| 20.9 | 4.25 | W–VS |
| 24.6 | 3.62 | W–M |
| 26.8 | 3.32 | W–VS |

[a]±0.15

Table IIA below shows the X-ray powder diffraction lines for calcined CIT-5 including actual relative intensities.

TABLE IIA

Calcined CIT-5

| 2 Theta[a] | d | Relative Intensity |
|---|---|---|
| 6.95 | 12.7 | 65–100 |
| 7.3 | 12.1 | 40–100 |
| 13.9 | 6.37 | 1–65 |
| 19.0 | 4.67 | 10–100 |
| 20.0 | 4.44 | 20–70 |
| 20.5 | 4.33 | 10–50 |
| 20.9 | 4.25 | 5–100 |
| 24.6 | 3.62 | 5–45 |
| 26.8 | 3.32 | 10–70 |

[a]±0.15

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.15 degrees.

The X-ray diffraction pattern of Table I is representative of "as-synthesized" or "as-made" CIT-5 zeolites. Minor variations in the diffraction pattern can result from variations in the, e.g., silica-to-alumina mole ratio of the particular sample due to changes in lattice constants. In addition, sufficiently small crystals will affect the shape and intensity of peaks, leading to significant peak broadening.

Representative peaks from the X-ray diffraction pattern of calcined CIT-5 are shown in Table II. Calcination can also result in changes in the intensities of the peaks as compared to patterns of the "as-made" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline CIT-5 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the CIT-5. The zeolite can also be impregnated with the metals, or, the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of CIT-5, the spatial arrangement of the atoms which form the basic crystal lattice of the zeolite remains essentially unchanged.

CIT-5 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

CIT-5 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

CIT-5 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which CIT-5 are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives. The CIT-5 catalysts may have high selectivity, and under hydrocarbon conversion conditions can provide a high percentage of desired products relative to total products.

CIT-5 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

Depending upon the type of reaction which is catalyzed, the zeolite may be predominantly in the hydrogen form, partially acidic or substantially free of acidity. As used herein, "predominantly in the hydrogen form" means that, after calcination, at least 80% of the cation sites are occupied by hydrogen ions and/or rare earth ions.

The following table indicates typical reaction conditions which may be employed when using catalysts comprising CIT-5 in the hydrocarbon conversion reactions of this invention. Preferred conditions are indicated in parentheses.

| Process | Temp., ° C. | Pressure | LHSV |
|---|---|---|---|
| Hydrocracking | 175–485 | 0.5–350 bar | 0.1–30 |
| Dewaxing | 200–475 (250–450) | 15–3000 psig (200–3000) | 0.1–20 (0.2–10) |
| Aromatics formation | 400–600 (480–550) | atm.-10 bar | 0.1–15 |
| Cat. cracking | 127–885 | subatm.-[1] (atm.-5 atm.) | 0.5–50 |
| Oligomerization | 232–649[2] 10–232[4] (27–204)[4] | 0.1–50 atm.[2,3] — — | 0.2–50[2] 0.05–20[5] (0.1–10)[5] |
| Paraffins to aromatics | 100–700 | 0–1000 psig | 0.5–40[5] |
| Condensation of alcohols | 260–538 | 0.5–1000 psig | 0.5–50[5] |
| Isomerization | 93–538 (204–315) | 50–1000 psig | 1–10 (1–4) |
| Xylene isomerization | 260–593[2] (315–566)[2] 38–371[4] | 0.5–50 atm.[2] (1–5 atm)[2] 1–200 atm.[4] | 0.1–100[5] (0.5–50)[5] 0.5–50 |

[1]Several hundred atmospheres
[2]Gas phase reaction
[3]Hydrocarbon partial pressure
[4]Liquid phase reaction
[5]WHSV Other reaction conditions and parameters are provided below.

Hydrocracking

Using a catalyst which comprises CIT-5, preferably predominantly in the hydrogen form, and a hydrogenation promoter, heavy petroleum residual feedstocks, cyclic stocks and other hydrockate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

CIT-5, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with CIT-5 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling above about 350° F.

A typical dewaxing process is the catalytic dewaxing of a hydrocarbon oil feedstock boiling above about 350° F. and containing straight chain and slightly branched chain hydrocarbons by contacting the hydrocarbon oil feedstock in the presence of added hydrogen gas at a hydrogen pressure of about 15–3000 psi with a catalyst comprising CIT-5 and at least one Group VIII metal.

The CIT-5 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

CIT-5 may also be utilized as a dewaxing catalyst in the form of a layered catalyst. That is, the catalyst comprises a first layer comprising zeolite CIT-5 and at least one Group VIII metal, and a second layer comprising an aluminosilicate zeolite which is more shape selective than zeolite CIT-5. The use of layered catalysts is disclosed in U.S. Pat. No. 5,149,421, issued Sep. 22, 1992 to Miller, which is incorporated by reference herein in its entirety. The layering may also include a bed of CIT-5 layered with a non-zeolitic component designed for either hydrocracking or hydrofinishing.

CIT-5 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig at space velocities (LHSV) between about 0.1 and 20 and a hydrogen recycle rate of about 400 to 1500 SCF/bbl. The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using CIT-5. For example, a $C_{20+}$ lube oil may be made by isomerizing a $C_{20+}$ olefin feed over a catalyst comprising CIT-5 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. and at a pressure of from about 15 psig to about 3000 psig in the presence of added hydrogen gas with a catalyst comprising CIT-5 in the hydrogen form and at least one Group VIII metal.

Aromatics Formation

CIT-5 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising CIT-5. It is also possible to convert heavier feeds into BTX or naphthalene derivatives of value using a catalyst comprising CIT-5.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium. The zeolite itself can be substantially free of acidity only at very high silica:alumina mole ratios.

Catalytic Cracking

Hydrocarbon cracking stocks can be catalytically cracked in the absence of hydrogen using CIT-5, preferably predominantly in the hydrogen form.

When CIT-5 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the CIT-5 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization

The present catalyst, preferably predominantly in the hydrogen form, is believed to be active and selective for isomerizing $C_4$ to $C_7$ hydrocarbons. The activity means that the catalyst can operate at relatively low temperature which thermodynamically favors highly branched paraffins. Consequently, the catalyst can produce a high octane product. The selectivity means that a relatively high liquid yield can be achieved when the catalyst is run at a high octane.

The present process comprises contacting the isomerization catalyst, i.e., a catalyst comprising CIT-5 in the hydrogen form, with a hydrocarbon feed under isomerization conditions. The feed is preferably a light straight run fraction, boiling within the range of 30° F. to 250° F. and preferably from 60° F. to 200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. No. 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

CIT-5 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising CIT-5.

CIT-5 can also be used for removing benzene from gasoline by alkylating the benzene as described above and removing the alkylated product from the gasoline.

For high catalytic activity, the CIT-5 zeolite should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene derivatives may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F, preferably 250° F. to 450° F. The reaction pressure should be sufficient to maintain at least a partial liquid phase in order to retard catalyst fouling. This is typically 50 psig to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hourly space velocity will range from about 0.1 to 10. U.S. Pat. No. 5,082,990 issued on Jan. 21, 1992 to Hsieh, et al. describes such processes and is incorporated herein by reference.

Isomerization of Olefins

CIT-5 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the CIT-5. The process may be carried out generally at a temperature from about 625° F. to about 950° F. (329–510° C.), for butenes, preferably from about 700° F. to about 900° F. (371–482° C.), and about 350° F. to about 650° F. (177–343° C.) for pentenes and hexenes. The pressure ranges from subatmospheric to about 200 psig, preferably from about 15 psig to about 200 psig, and more preferably from about 1 psig to about 150 psig.

The liquid hourly space velocity during contacting is generally from about 0.1 to about 50 hr$^{-1}$, based on the hydrocarbon feed, preferably from about 0.1 to about 20 hr$^{-1}$, more preferably from about 0.2 to about 10 hr$^{-1}$, most preferably from about 1 to about 5 hr$^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Conversion of Paraffins to Aromatics

CIT-5 can be used to convert light gas $C_2$–$C_6$ paraffins to higher molecular weight hydrocarbons including aromatic compounds. Preferably, the zeolite will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Xylene Isomerization

CIT-5 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt % of a diluent such as toluene, trimethylbenzene, naphthenes or paraffins.

Oligomerization

It is expected that CIT-5 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising CIT-5.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Condensation of Alcohols

CIT-5 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Other Uses for CIT-5

CIT-5 can also be used as an adsorbent with high selectivities based on molecular sieve behavior and also based upon preferential hydrocarbon packing within the pores.

CIT-5 may also be used for the catalytic reduction of the oxides of nitrogen in a gas stream. Typically, the gas stream also contains oxygen, often a stoichiometric excess thereof. Also, the CIT-5 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a zeolite is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

EXAMPLES

The following examples demonstrate but do not limit the present invention.

Example 1

Synthesis of N(16) methylsparteinium hydroxide (MeSPAOH)

21.1 Grams (50 mmol) of (−) sparteine sulfate pentahydrate (Aldrich) is added to 50 ml of a 3 M NaOH solution. The resulting suspension is stirred until the crystals are completely dissolved and two phases form. The organic phase is extracted three times with 25 ml portions of diethyl ether and the combined extracts are dried over solid KOH (85%) and filtered. The solvent is then evaporated at room temperature under vacuum. The recovered (−) sparteine is dissolved in 100 ml of acetone containing 28.3 g (1.5 equiv.) of methyl iodide. The resulting reaction mixture is stirred in the dark for 24 hours. and the yellow solid product which forms is filtered after the addition of 50 ml of diethyl ether. The recovered solid (15.2 g, 81% yield) is recrystallized twice in 2-propanol by adding ethyl acetate until turbidity to give 13.7 g (73% yield) of slightly yellow crystals. Analyses: Calculated for $C_{16}N_2H_{29}I$: C, 51.1%; N, 7.4%; H, 7.7%; I, 33.8%. Found: C, 51.0%; N, 7.4%; H, 7.9%; I, 33.7%. The IR spectrum of the product agrees with a previously reported spectrum for N(16) methylsparteinium iodide.

Amberlite IRA-400(Cl) (Aldrich) anion exchange resin, exchanged to the bromide form, is used to convert the iodide salt prepared as above to the corresponding bromide. Typically, 7.52 g of N(16) methylsparteinium iodide (20 mmol) is dissolved in 50 ml of water and exchanged in an ion exchange column containing 100 ml of anion exchange resin (with 140 mmol of exchange capacity). After washing the column with an additional 200 ml of distilled water, the aqueous solution obtained is evaporated in a rotavapor until dryness and recrystallized as described above from 2-propanol-ethyl acetate. Elemental analyses indicate a yield of 95% for the bromide form. Similarly, the hydroxide form is obtained using Amberlite IRA-400 (OH) anion exchange resin. After exchange, the aqueous solution is concentrated to 50 ml. The yield is 92.8% based on titration of the resultant solution and gives a concentration of 0.371 M of N(16) methylsparteinium hydroxide.

Example 2

Preparation of Silicate CIT-5

0.018 Gram of LiOH anhydrous powder is dissolved in 2.54 g of distilled water. To the resulting solution is added 2.21 g of N(16) methylsparteinium hydroxide (MeSPAOH) solution (18.2 wt %) and the resulting reaction mixture is stirred for 10 minutes. $SiO_2$ (Ludox HS-30 from E. I. duPont), 1.5 g, is added to the reaction mixture and the mixture is stirred for two hours. The resulting gel is divided into portions and heated in three quartz tubes at 175° C. for 7 days, 10 days and 11 days at autogenous pressure. The product is recovered by vacuum filtration and determined by X-ray diffraction (XRD) to be CIT-5 (the product recovered after 10 days also contains some amorphous material).

Typical XRD lines for the as-made (i.e., uncalcined) product of this example is indicated in Table III below.

TABLE III

| 2 Theta | d | $I/I_0 \times 100$ |
|---|---|---|
| 6.957 | 12.695 | 77 |
| 7.288 | 12.119 | 50 |
| 12.810 | 6.905 | 4 |

TABLE III-continued

| 2 Theta | d | I/I₀ × 100 |
|---|---|---|
| 13.929 | 6.353 | 37 |
| 17.093 | 5.183 | 3 |
| 18.963 | 4.676 | 100 |
| 19.588 | 4.529 | 25 |
| 20.001 | 4.436 | 57 |
| 20.499 | 4.329 | 40 |
| 20.953 | 4.236 | 60 |
| 21.770 | 4.079 | 3 |
| 21.931 | 4.050 | 8 |
| 22.613 | 3.929 | 7 |
| 23.410 | 3.797 | 13 |
| 24.218 | 3.672 | 6 |
| 24.625 | 3.612 | 34 |
| 25.796 | 3.451 | 5 |
| 26.097 | 3.412 | 7 |
| 26.733 | 3.332 | 59 |
| 27.116 | 3.286 | 18 |
| 28.224 | 3.159 | 28 |
| 29.378 | 3.038 | 4 |
| 29.818 | 2.994 | 6 |
| 31.374 | 2.849 | 11 |
| 31.550 | 2.833 | 4 |
| 32.990 | 2.713 | 6 |
| 33.980 | 2.636 | 5 |
| 35.330 | 2.539 | 4 |
| 35.636 | 2.517 | 10 |
| 36.417 | 2.465 | 7 |
| 37.027 | 2.426 | 5 |
| 37.700 | 2.384 | 4 |
| 38.731 | 2.323 | 4 |
| 44.699 | 2.026 | 11 |
| 49.424 | 1.843 | 4 |

Example 3

Synthesis of CIT-5 in the Presence of Zinc

In a manner similar to that described in Example 2, CIT-5 is made from the following components:

0.012 g LiOH 1.70 g distilled water 1.47 g MeSPAOH solution (18.2 wt %)

0.043 g $Zn(CH_3COO)_2 2H_2O$ 1.0 g $SiO_2$ (Ludox HS-30)

This produces a gel composition, in terms of mole ratios, as follows:

0.1 LiOH:0.04 $Zn(CH_3COO)_2 2H_2O$:0.2 MeSPAOH:$SiO_2$:40 $H_2O$

Product is recovered by vacuum filtration after 13 days and 15 days, and determined by XRD to be CIT-5 (the product recovered after 15 days also contains some unknown material).

Typical XRD lines for the as-made product of this example is indicated in Table IV below.

TABLE IV

| 2 Theta | d | I/I₀ × 100 |
|---|---|---|
| 6.903 | 12.794 | 17 |
| 7.268 | 12.152 | 43 |
| 12.001 | 7.368 | 7 |
| 12.846 | 6.886 | 5 |
| 13.841 | 6.393 | 9 |
| 14.597 | 6.064 | 3 |
| 16.331 | 5.423 | 34 |
| 18.930 | 4.684 | 61 |
| 19.641 | 4.516 | 40 |

TABLE IV-continued

| 2 Theta | d | I/I₀ × 100 |
|---|---|---|
| 19.967 | 4.443 | 58 |
| 20.432 | 4.343 | 40 |
| 20.826 | 4.262 | 21 |
| 21.590 | 4.113 | 30 |
| 21.963 | 4.044 | 18 |
| 23.348 | 3.807 | 8 |
| 24.208 | 3.674 | 3 |
| 24.548 | 3.623 | 20 |
| 25.878 | 3.440 | 11 |
| 26.799 | 3.324 | 100 |
| 27.146 | 3.282 | 23 |
| 28.129 | 3.170 | 25 |
| 29.964 | 2.990 | 3 |
| 30.209 | 2.958 | 2 |
| 31.276 | 2.858 | 6 |
| 31.625 | 2.827 | 3 |
| 32.913 | 2.719 | 4 |
| 33.462 | 2.676 | 5 |
| 33.719 | 2.656 | 4 |
| 35.569 | 2.522 | 20 |
| 36.265 | 2.475 | 8 |
| 37.051 | 2.424 | 6 |
| 37.848 | 2.375 | 5 |
| 38.646 | 2.328 | 3 |
| 44.625 | 2.029 | 4 |
| 44.828 | 2.020 | 6 |
| 47.102 | 1.928 | 4 |
| 49.616 | 1.836 | 5 |

After the product is calcined, it has the XRD lines indicated in Table V below.

TABLE V

| 2 Theta | d | I/I₀ × 100 |
|---|---|---|
| 6.913 | 12.777 | 39 |
| 7.305 | 12.092 | 100 |
| 12.224 | 7.235 | 7 |
| 12.921 | 6.846 | 13 |
| 13.830 | 6.398 | — |
| 13.917 | 6.358 | — |
| 18.995 | 4.668 | 41 |
| 19.754 | 4.491 | 21 |
| 20.044 | 4.426 | 60 |
| 20.503 | 4.328 | 47 |
| 20.864 | 4.254 | 17 |
| 21.295 | 4.169 | 10 |
| 21.645 | 4.102 | 28 |
| 22.103 | 4.018 | 10 |
| 22.568 | 3.937 | 2 |
| 23.409 | 3.797 | 6 |
| 24.319 | 3.657 | 7 |
| 24.612 | 3.614 | 13 |
| 26.016 | 3.422 | 7 |
| 26.172 | 3.402 | 3 |
| 26.944 | 3.306 | 57 |
| 27.282 | 3.266 | 16 |
| 28.059 | 3.178 | 6 |
| 28.222 | 3.160 | 18 |
| 29.910 | 2.985 | 3 |
| 30.254 | 2.952 | 1 |
| 31.393 | 2.847 | 5 |
| 31.778 | 2.814 | 1 |
| 33.020 | 2.710 | 4 |
| 33.589 | 2.666 | 2 |
| 33.876 | 2.644 | 0 |
| 34.358 | 2.608 | 1 |
| 35.702 | 2.513 | 21 |
| 36.289 | 2.474 | 3 |
| 36.427 | 2.465 | 6 |
| 37.233 | 2.413 | 5 |
| 38.024 | 2.365 | 3 |
| 38.807 | 2.319 | 1 |
| 43.680 | 2.070 | 2 |

TABLE V-continued

| 2 Theta | d | I/I$_0$ × 100 |
|---|---|---|
| 44.596 | 2.030 | 1 |
| 45.017 | 2.012 | 4 |
| 45.921 | 1.975 | 1 |
| 47.293 | 1.921 | 3 |
| 48.250 | 1.885 | 0 |
| 48.846 | 1.863 | 0 |
| 49.869 | 1.827 | 3 |
| 50.537 | 1.805 | 3 |

Example 4

Synthesis of Aluminosilicate CIT-5

In a manner similar to that described in Example 2, aluminosilicate CIT-5 is made from the following components:

0.018 g LiOH 3.47 g distilled water 1.27 g MeSPAOH solution (31.0 wt %)

0.028 g Al(NO$_3$)$_3$9H$_2$O 1.50 g SiO$_2$ (Ludox HS-30)

This produces a gel composition, in terms of mole ratios, as follows:

0.1 LiOH:0.01 Al(NO$_3$)$_3$9H$_2$O:0.2 MeSPAOH:SiO$_2$:40 H$_2$O

Product is recovered by vacuum filtration after 7 days and 9 days, and determined by XRD to be CIT-5.

Typical XRD lines for the as-made product of this example is indicated in Table VI below.

TABLE VI

| 2 Theta | d | I/I$_0$ × 100 |
|---|---|---|
| 6.334 | 13.942 | 3 |
| 7.000 | 12.617 | 100 |
| 7.287 | 12.122 | 25 |
| 12.650 | 6.992 | 2 |
| 12.825 | 6.897 | 3 |
| 13.010 | 6.799 | 2 |
| 13.361 | 6.621 | 2 |
| 13.972 | 6.333 | 58 |
| 14.590 | 6.066 | 3 |
| 18.170 | 4.878 | 3 |
| 18.323 | 4.838 | 3 |
| 18.992 | 4.669 | 73 |
| 19.599 | 4.526 | 18 |
| 20.032 | 4.429 | 41 |
| 20.523 | 4.324 | 31 |
| 20.996 | 4.228 | 99 |
| 21.800 | 4.074 | 3 |
| 21.981 | 4.041 | 6 |
| 23.447 | 3.791 | 9 |
| 24.251 | 3.667 | 5 |
| 24.655 | 3.608 | 31 |
| 25.393 | 3.505 | 4 |
| 25.802 | 3.450 | 3 |
| 26.104 | 3.411 | 4 |
| 26.749 | 3.330 | 45 |
| 27.148 | 3.282 | 13 |
| 28.130 | 3.170 | 22 |
| 28.234 | 3.158 | 23 |
| 29.836 | 2.992 | 3 |
| 31.374 | 2.849 | 8 |
| 33.065 | 2.707 | 4 |
| 33.481 | 2.674 | 4 |
| 35.308 | 2.540 | 3 |
| 35.675 | 2.515 | 8 |

TABLE VI-continued

| 2 Theta | d | I/I$_0$ × 100 |
|---|---|---|
| 36.492 | 2.460 | 7 |
| 37.007 | 2.427 | 4 |
| 37.744 | 2.382 | 4 |
| 38.796 | 2.319 | 3 |
| 44.750 | 2.024 | 9 |
| 47.198 | 1.924 | 3 |
| 49.639 | 1.835 | 2 |

After the product is calcined, it has the XRD lines indicated in Table VII below.

TABLE VII

| 2 Theta | d | I/I$_0$ × 100 |
|---|---|---|
| 6.922 | 12.760 | 100 |
| 7.301 | 12.098 | 86 |
| 12.235 | 7.228 | 11 |
| 12.920 | 6.847 | 6 |
| 13.869 | 6.380 | 7 |
| 17.105 | 5.180 | — |
| 17.161 | 5.163 | 1 |
| 18.515 | 4.788 | 1 |
| 18.989 | 4.670 | 40 |
| 19.730 | 4.496 | 11 |
| 20.041 | 4.427 | 31 |
| 20.510 | 4.327 | 26 |
| 20.876 | 4.252 | 26 |
| 23.437 | 3.793 | 5 |
| 24.301 | 3.660 | 4 |
| 24.613 | 3.614 | 18 |
| 25.235 | 3.526 | 2 |
| 26.008 | 3.423 | 3 |
| 26.147 | 3.405 | 4 |
| 26.923 | 3.309 | 29 |
| 27.268 | 3.268 | 8 |
| 27.947 | 3.190 | 4 |
| 28.222 | 3.160 | 16 |
| 29.887 | 2.987 | 1 |
| 30.223 | 2.955 | 1 |
| 31.367 | 2.850 | 5 |
| 31.796 | 2.812 | 1 |
| 32.232 | 2.775 | 1 |
| 33.010 | 2.711 | 3 |
| 33.563 | 2.668 | 2 |
| 33.849 | 2.646 | 1 |
| 34.345 | 2.609 | 1 |
| 35.152 | 2.551 | — |
| 35.690 | 2.514 | 7 |
| 36.337 | 2.470 | 4 |
| 37.208 | 2.415 | 3 |
| 37.591 | 2.391 | 1 |
| 38.018 | 2.365 | 2 |
| 38.757 | 2.322 | 1 |
| 39.350 | 2.288 | — |
| 40.031 | 2.251 | — |
| 40.782 | 2.211 | — |
| 41.103 | 2.194 | — |
| 41.957 | 2.152 | — |
| 42.892 | 2.107 | 1 |
| 43.694 | 2.070 | 1 |
| 44.581 | 2.031 | 2 |
| 44.997 | 2.013 | 2 |
| 45.937 | 1.974 | 1 |
| 47.281 | 1.921 | 2 |
| 48.265 | 1.884 | — |
| 48.863 | 1.862 | — |
| 49.857 | 1.828 | 2 |
| 50.562 | 1.804 | 3 |

Example 5

Synthesis of Aluminosilicate CIT-5

In a manner similar to that described in Example 2, aluminosilicate CIT-5 is made from the following components:

0.18 g LiOH
3.47 g distilled water
1.27 g MeSPAOH solution (31.0 wt %)
0.048 g Al(NO$_3$)$_3$9H$_2$O
1.5 g SiO$_2$ (Ludox HS-30)
This produces a gel composition, in terms of mole ratios, as follows:

0.1 LiOH:0.02 Al(NO$_3$)$_3$:0.2 MeSPAOH:SiO$_2$:40 H$_2$O

Product is recovered after 21 days and determined by XRD to be a mixture of amorphous material and CIT-5.

Comparative Example A

Attempted Synthesis of Aluminosilicate CIT-5

In a manner similar to that described in Example 2, aluminosilicate CIT-5 is made from the following components:

0.18 g LiOH
3.35 g distilled water
1.27 g MeSPAOH solution (31.0 wt %)
0.281 g Al(NO$_3$)$_3$9H$_2$O
1.5 g SiO$_2$ (Ludox HS-30)
This produces a gel composition, in terms of mole ratios, as follows:

0.1 LiOH:0.1 Al(NO$_3$)$_3$:0.2 MeSPAOH:SiO$_2$:40 H$_2$O

Product is recovered after 60 days and determined by XRD to be amorphous material.

Example 6

Synthesis of Borosilicate CIT-5

In a manner similar to that described in Example 2, borosilicate CIT-5 is made from the following components:

0.18 g LiOH
3.47 g distilled water
1.27 g MeSPAOH solution (31.0 wt %)
0.0046 g H$_3$BO$_3$
1.5 g SiO$_2$ (Ludox HS-30)
This produces a gel composition, in terms of mole ratios, as follows:

0.1 LiOH:0.01 H$_3$BO$_3$:0.2 MeSPAOH:SiO$_2$:40 H$_2$O

Product is recovered after 7 days and determined by XRD to be CIT-5.

Example 7

Synthesis of Gallosilicate CIT-5

In a manner similar to that described in Example 2, gallosilicate CIT-5 is made from the following components:

0.18 g LiOH
3.47 g distilled water
1.27 g MeSPAOH solution (31.0 wt %)
0.019 g Ga(NO$_3$)$_3$xH$_2$O (x=3.4)
1.5 g SiO$_2$ (Ludox HS-30)
This produces a gel composition, in terms of mole ratios, as follows:

0.1 LiOH:0.01 Ga(NO$_3$)$_3$:0.2 MeSPAOH:SiO$_2$:40 H$_2$O

Product is recovered after 7 days and determined by XRD to be CIT-5.

Example 8

Synthesis of Silicate CIT-5

In a manner similar to that described in Example 2, silicate CIT-5 is synthesized in a Teflon lined autoclave instead of quartz tubes from the following components:

0.19 g LiOH
4.22 g distilled water
0.86 g MeSPAOH solution (49.8 wt %)
1.6 g SiO$_2$ (Ludox HS-30)
This produces a gel composition, in terms of mole ratios, as follows:

0.1 LiOH:0.2 MeSPAOH:SiO$_2$:40 H$_2$O

Product is recovered after 6 days and determined by XRD to be CIT-5.

Example 9

Synthesis of Silicate CIT-5 Using Li and Na

In a manner similar to that described in Example 8, silicate CIT-5 is synthesized from the following components:

6 0.14 g LiOH
0.016 g 50 wt % aqueous NaOH solution
4.22 g distilled water
0.86 g MeSPAOH solution (49.8 wt %)
1.6 g SiO$_2$ (Ludox HS-30)
This produces a gel composition, in terms of mole ratios, as follows:

0.075 LiOH:0.025 NaOH:0.2 MeSPAOH:SiO$_2$:40 H$_2$O

Product is recovered after 5 days and determined by XRD to be CIT-5.

Example 10

Synthesis of Silicate CIT-5 Using Li and K

In a manner similar to that described in Example 8, silicate CIT-5 is synthesized from the following components:

0.14 g LiOH
0.022 g 50 wt % aqueous KOH solution
4.22 g distilled water
0.86 g MeSPAOH solution (49.8 wt %)
1.6 g SiO$_2$ (Ludox HS-30)
This produces a gel composition, in terms of mole ratios, as follows:

0.075 LiOH:0.025 KOH:0.2 MeSPAOH:SiO$_2$:40 H$_2$O

Product is recovered after 5 days and determined by XRD to be CIT-5 and amorphous material.

Example 11

Synthesis of Aluminosilicate CIT-5

In the Teflon cup for a small Parr reactor is combined 3.4 grams of a 0.66 M solution of MeSPAOH template with 8.5 grams of water and 0.06 gram of lithium carbonate. 0.90 Gram of 390-HUA Y zeolite (sold by Tosoh) is added as a source of both silicon and aluminum. The reactor is sealed and heated at 160° C. while being tumbled at 43 RPM for a period of 12 days. Upon cooling the reactor, the solid product is collected by filtration, washed and dried. The product is determined by XRD to be CIT-5.

The CIT-5 product is calcined and ammonium ion exchanged as previously described.

Example 12

Preparation of Pd CIT-5

0.99 Gram of the ammonium exchanged CIT-5 prepared in Example 11 is slurried into 9 ml of water and 2 ml of a 0.156 N ammonium hydroxide solution. A solution of palladium tetraamine dinitrate buffered in ammonium hydroxide is then added. The quantity of palladium is sufficient to provide 0.50 wt % Pd on the CIT-5 if completely ion exchanged onto the zeolite. The zeolite and solution are allowed to stand for several days at room temperature, after which the zeolite is filtered and washed. This product is then calcined at 482° C. after a slow ramp to 120° C. followed by a 1 degree increase to 482° C. The zeolite is held at 482° C. for three hours.

Example 13

Hydrocracking and Hydroisomerization of n-Hexadecane

Using Pd CIT-5

0.50 Gram of the Pd CIT-5 prepared in Example 12 is pressed into a tablet at 3000 psi, fractrued, meshed to 20–40, and loaded into a stainless steel reactor. The zeolite is dried in situ and the reactor temperature is brought to 600° F. (315° C.) and pressurized to 1200 psi hydrogen flow. A n-hexadecane feed is introduced at 1.00 microliter/minute. At 167 hours on stream and at 660° F. (349° C.), the catalyst is achieving 96% conversion. The liquid to gas ratio of the converted products is 5.3. Iso/normal ratios for the gasoline fractions and hexadecane are given below.

| Carbon No. | Iso/Normal ratio |
|---|---|
| 4 | 1.95 |
| 5 | 3.19 |
| 6 | 2.89 |
| 7 | 3.52 |
| 8 | 4.20 |
| 9 | 4.69 |
| 10 | 5.82 |
| 16 | 7.87 |

Example 14

Adsorption Properties of CIT-5

A sample of silicate CIT-5 from Example 2 (crystallized for 11 days) is calcined by heating it from room temperature to 700° C. over a period of three hours and maintaining it at 700° C. for an additional two hours. The calcined sample's adsorption properties are determined by a McBain Baker balance. The resulting adsorption properties are—cyclohexane: 0.07 ml/g 2,2-dimethylpropane: 0.05 ml/g.

Example 15

Reactions of m-Xylene Over CIT-5

CIT-5 with a Si/Al mole ratio of about 200 is pressed into a wafer. The wafer is then crushed into small pellets. The pellets are size sorted, and only pellets of the size −35/+70 are used. 100–150 Milligrams of the catalyst is placed in a downward flow reactor. The catalyst is pretreated in a flow of helium at 50 ml/min. with the following temperature program:

$$RT \xrightarrow{2\ hr} 175°\ C. \xrightarrow{2\ hr} 175°\ C. \xrightarrow{1.5\ hr} 350°\ C. \xrightarrow{3\ hr} 350°\ C.$$

The temperature is the decreased to 317° C. over 25 minutes and then maintained at this temperature for the reaction. The helium flow is reduced to 20 ml/min. and directed through a saturator containing m-xylene (Aldrich 99+%) which is kept at 10° C. (±0.5° C.). The vapor pressure of m-xylene at this temperature is 3.4 torr. The helium/m-xylene stream is then passed over the catalyst bed for reaction. Products are analyzed with an on-line gas chromatograph. The results are indicated below.

Catalyst mass=116.2 mg

Initial conversion=2.5%

Para/Ortho=0.9

Isomerization/Disproportionation=11

Only 1,2,4 trimethylbenzene is formed, although this is likely due to the low conversion. The 1,3,5 isomer is detected by the gas chromatograph, but the amount of this material is too small to be integrated by the gas chromatograph's integrator.

What is claimed is:

1. A zeolite comprising an oxide of a tetravalent element or mixture of oxides of tetravalent elements and, optionally, an oxide of a trivalent element or mixtures of oxides of trivalent elements and having, after calcination, the X-ray diffraction lines of Table II.

2. A zeolite comprising an oxide selected from the group consisting of silicon oxide, germanium oxide and mixtures thereof and an optional oxide selected from aluminum oxide, boron oxide, gallium oxide, iron oxide and mixtures thereof, and having, after calcination, the X-ray diffraction lines of Table II.

3. A zeolite according to claim 2 wherein the oxides comprise silicon oxide and aluminum oxide.

4. A zeolite according to claim 2 wherein the oxides comprise silicon oxide and boron oxide.

5. A zeolite according to claim 2 wherein the oxides comprise silicon oxide and gallium oxide.

6. A zeolite comprising an oxide of silicon, germanium or mixtures thereof and an oxide of titanium and having, after calcination, the X-ray diffraction lines of Table II.

7. A zeolite according to claim 1 wherein said zeolite is predominantly in the hydrogen form.

8. A zeolite according to claim 1 wherein said zeolite is substantially free of acidity.

9. A zeolite having a composition, as synthesized and in the anhydrous state, in terms of mole ratios as follows:

$YO_2/W_aO_b > 40$ $M/YO_2 \leq 0.05$ $Q/YO_2 \leq 0.05$ wherein Y is silicon, germanium or a mixture thereof; W is aluminum, boron, gallium, iron or mixtures thereof; a=1 or 2, b=2 when a=1 and b=3 when a=2; M is an alkali metal; and Q comprises a N(16) methylsparteinium cation, and having, after calcination, the X-ray diffraction lines of Table II.

10. A zeolite according to claim 9 wherein W is aluminum and Y is silicon.

11. A zeolite according to claim 9 wherein W is boron and Y is silicon.

12. A zeolite according to claim 9 wherein W is gallium and Y is silicon.

13. A zeolite having a composition, as synthesized and in the anhydrous state, in terms of mole ratios as follows:

$YO_2/TiO_2 > 40$ $M/YO_2 \leq 0.05$ $Q/YO_2 \leq 0.05$ wherein Y is silicon, germanium or a mixture thereof; M is an alkali metal; and Q comprises a N(16) methylsparteinium cation, and having, after calcination, the X-ray diffraction lines of Table II.

14. A method of preparing a crystalline material comprising an oxide of a tetravalent element or mixture of oxides of tetravalent elements and, optionally, an oxide of a trivalent element or mixtures of oxides of trivalent elements, and having, after calcination, the X-ray diffraction pattern lines of Table II, said method comprising contacting in admixture under crystallization conditions sources of said oxides, a source of alkali metal comprising lithium, and a templating agent comprising a N(16) methylsparteinium cation.

15. The method according to claim 14 wherein the tetravalent element is selected from the group consisting of silicon, germanium and combinations thereof.

16. The method according to claim 14 wherein the trivalent element is selected from the group consisting of aluminum, boron, gallium, iron and mixtures thereof.

17. The method according to claim 14 wherein the tetravalent element is silicon and the trivalent element is aluminum.

18. The method according to claim 14 wherein the tetravalent element is silicon and the trivalent element is boron.

19. The method according to claim 14 wherein the tetravalent element is silicon and the trivalent element is gallium.

20. The method according to claim 14 wherein the tetravalent element is silicon and the trivalent element is iron.

21. The method of claim 14 wherein the source of the alkali metal contains no alkali metal other than lithium.

22. The method of claim 14 wherein the source of alkali metal contains lithium and another alkali metal.

23. The method of claim 14 wherein the admixture further comprises a source of zinc.

24. A method of preparing a crystalline material comprising an oxide of a tetravalent element or mixture of oxides of tetravalent elements and, optionally, an oxide of a trivalent element or mixtures of oxides of trivalent elements, and having, after calcination, the X-ray diffraction lines of Table II, said method comprising contacting in admixture under crystallization conditions sources of said oxides, a source of alkali metal and a templating agent comprising a N(16) methylsparteinium cation.

25. The method according to claim 24 wherein the tetravalent element is selected from the group consisting of silicon, germanium and combinations thereof.

26. The method according to claim 24 wherein the trivalent element is selected from the group consisting of aluminum, boron, gallium, iron and mixtures thereof.

27. The method according to claim 24 wherein the tetravalent element is silicon and the trivalent element is aluminum.

28. The method according to claim 24 wherein the tetravalent element is silicon and the trivalent element is boron.

29. The method according to claim 24 wherein the tetravalent element is silicon and the trivalent element is gallium.

30. The method according to claim 24 wherein the tetravalent element is silicon and the trivalent element is iron.

31. The method of claim 24 wherein the source of the alkali metal contains no alkali metal other than lithium.

32. The method of claim 24 wherein the source of alkali metal contains lithium and another alkali metal.

33. The method of claim 24 wherein the admixture further comprises a source of zinc.

* * * * *